United States Patent [19]

Dvorsky et al.

[11] Patent Number: 4,634,917
[45] Date of Patent: Jan. 6, 1987

[54] ACTIVE MULTI-LAYER PIEZOELECTRIC TACTILE SENSOR APPARATUS AND METHOD

[75] Inventors: James E. Dvorsky, Norwich Township, Ohio; Brian A. Kelley, Bethesda, Md.; Robert B. McCown, Upper Arlington; G. Frederick Renner, Clinton Township, both of Ohio

[73] Assignee: Battelle Memorial Institute, Columbus, Ohio

[21] Appl. No.: 686,124

[22] Filed: Dec. 26, 1984

[51] Int. Cl.⁴ .......................................... H01L 41/08
[52] U.S. Cl. .................................... 310/328; 310/323; 310/338; 310/339; 310/366; 310/800
[58] Field of Search ............... 310/311, 328, 338, 339, 310/366, 800, 322, 323, 325, 334; 340/365 A

[56] References Cited

U.S. PATENT DOCUMENTS

| | | | |
|---|---|---|---|
| 3,229,387 | 1/1966 | Linvill | 310/332 X |
| 3,401,377 | 10/1968 | Bartlett et al. | 310/328 X |
| 3,732,389 | 5/1973 | Kaelin et al. | 340/365 A X |
| 3,935,485 | 1/1976 | Yoshida et al. | 310/339 |
| 4,071,785 | 1/1978 | Yoshida | 310/800 X |
| 4,234,813 | 11/1980 | Iguchi et al. | 310/339 X |
| 4,328,441 | 5/1982 | Kroeger et al. | 310/339 X |
| 4,354,132 | 10/1982 | Borburgh et al. | 310/800 X |
| 4,356,422 | 10/1982 | Van Maanen | 310/800 X |
| 4,394,773 | 7/1983 | Ruell | 310/800 X |
| 4,491,760 | 1/1985 | Linvill | 310/800 X |
| 4,495,434 | 1/1985 | Diepers et al. | 340/365 A X |

Primary Examiner—Mark O. Budd
Attorney, Agent, or Firm—Klaus H. Wiesmann

[57] ABSTRACT

A tactile sensing apparatus having a piezoelectric energizing layer with a plurality of conductors disposed on one surface of a piezoelectric material and a plurality of conductors disposed on the opposite surface of the piezoelectric material, the plurality of conductors having electrical connections connected to electrical energizing means. An electrical insulating layer disposed adjacent the piezoelectric energizing layer. A second piezoelectric sensing layer is disposed adjacent the insulating layer, and has conducting surfaces disposed on opposite surfaces thereof. The conductors in the piezoelectric energizing layer provide N×M energizing areas with N+M electrical connections to the energizing layer. Further apparatus may include an oscillator, an optional amplifier and a switching means or multiplexer for the input signal.

The apparatus may optionally have more than one piezoelectric energizing layer as well as more than one piezoelectric sensing layer. PVF$_2$ is the preferred piezoelectric material. An optional base material and protective layer may be used.

A method of operating the tactile sensor includes providing a variable frequency electrical signal at a frequency and amplitude adapted to energize the energizing areas. The signal is switched to the conductors to energize selected energizing areas of the energizing layer in a predetermined sequence. The signal generated in the sensing layer that varies in frequency and amplitude in response to an object in contact with the tactile sensor is processed for frequency and amplitude information to determine the characteristics of the object such as shape, force or weight.

60 Claims, 8 Drawing Figures

ACTIVE MULTI-LAYER PIEZOELECTRIC TACTILE SENSOR APPARATUS AND METHOD

FIELD OF THE INVENTION

This invention relates to a tactile sensor and a sensing method that can be used to detect contact between the sensor and another object. Some of the properties that can be sensed are shape, texture, pressure, position and orientation. The sensor and sensing method have utility in industrial machinery, robots, medical devices and prosthetic devices.

BACKGROUND OF THE INVENTION

Robotic devices and systems are finding increased usage in a variety of applications. They extend into the realms of medicine (e.g. prosthetic devices), military applications, industrial robots (for assembly), hazardous industrial environments and so on.

For a robotic device to operate intelligently within a given but flexible and changing environment, it must be able to accurately determine, or sense, what its surroundings are. Advanced sensory capabilities will characterize the next generation of robots, and among these sensory functions is tactile sensing, the ability to determine physical features through touch mechanisms. Although the goal can be stated quite simply, the technological implementation presents quite another challenge. Furthermore, the tactile sensing capability is a broad spectrum: at one end of the spectrum is the ability to merely detect the presence of an object, and at the other end is the ability to determine the surface texture of an object. Rounding out the spectrum is the ability to determine an object's size and shape and whether or not it has moved on the sensor's surface.

An example of a piezoelectric device is U.S. Pat. No. 4,328,441 (Kroeger, et al) and its international counterpart W0 No. 81/02223. These reveal a layered structure having piezoelectric polymer films on opposite sides of an insulating layer for the purpose of providing a keyboard. This does not avoid the phantom point problem.

IBM Technical Bulletin, Vol. 20, No. 1, J. P. Dahl, June 1977, reveals a scanned piezoelectric keyboard switch where each key is chosen to have a unique inherent resonant frequency while the switches are wired in parallel. Contact dampens the frequency and the impedance of the undampened crystal changes greatly.

IBM Technical Bulletin, Vol. 20, No. 7, J. Fajans, December 1977, discloses an acoustical touch panel in which acoustic plane wave impulses are generated at fixed times in orthogonal directions by two long piezoelectric crystals mounted on adjacent sides of a lower plate. Local acoustical coupling is said to result in a spherical wave originating from the point of contact in an upper plate when an impulse is present in the lower plate.

P. Dario et al, "Touch Sensitive Polymer Skin Uses Piezoelectric Properties to Recognize Orientation of Objects", an article in Sensor Review p. 194–198, Oct. 1982, use a single layer polyvinylidene fluoride $PVF_2$ sensor with 256 sensing areas (16×16 array) to recognize object orientation. One lead pin is required for each sensing area.

A bilaminate $PVF_2$ sensor is proposed in "Piezo-Pyroelectric Polymers Skin-Like Tactile Sensors for Robots and Prostheses", 13th *Symposium 7 Conference and Exposition* on Industrial Robots and Robots, Chicago, R. Bardelli et al, April 1983, where the outer layer senses temperature and the inner senses mechanical forces. The article teaches against row by column reading involving multiplexing. A lead for each sensing area is advocated.

In "Piezoelectric Polymers: New Sensor Materials for Robotic Applications", 13th Symposium on Industrial Robots and *Robots 7 Conference and Exposition Chicago,* P. Dario et al April 1983, various $PVF_2$ contact sensors and touch sensors are described. The touch sensor using 256 sensor regions has at least 256 leads. A tactile sensor using a $PVF_2$ emitter and receiver uses the time of flight of ultrasonic waves through a compliant material to measure pressure on the sensor.

In the prior art there are several major disadvantages that are overcome by the present invention. First the location, shape, and pressure of an object can be actively sensed. Secondly, switching noise problems are overcome by multiplexing the energizing signal rather than the sensing signal. Third, the invention avoids the "phantom point" problem of a crossed array. Fourth, great sensitivity and high resolution are possible. Finally, the complexity of the lead array can be greatly reduced by allowing the use of N+M leads to address N×M active areas.

BRIEF DESCRIPTION OF THE INVENTION

In accordance with the invention there is provided an apparatus for tactile sensing. One embodiment of the apparatus is basically a sandwich structure of several layers. A first layer of piezoelectric energizing material is used to interrogate the sensing layers. The first layer may have parallel conductors or electrodes on two sides thereof with rows of conductors on one side and columns of conductors on the other. Other patterns can be used but this pattern was found useful for multiplexing techniques.

An insulating layer separates the piezoelectric energizing layer from a piezoelectric sensing layer that is used as a signal source to detect pressure on the apparatus. The sensing layer may contain two conducting layers on opposing sides of a piezoelectric material. $PVF_2$ is the material of choice for the piezoelectric material for both the energizing and sensing layer. A base material and outer protective layer, may optionally be a part of the design as well as a multiplexer that is integral with the sensor.

Unlike conventional tactile sensors, this tactile sensor has both a static and dynamic response. When an object contacts the transducer, the sensing layer is flexed, generating a small output transient voltage. However, by continuously AC stimulating areas on the energizing layer (defined by the intersection of one row conductor and one column conductor), an acoustic wave is transmitted through the insulating layer, which in turn stimulates the sensing layer. The output is then a continuous AC signal with a frequency equal to the stimulating frequency and an amplitude corresponding to the efficiency of acoustic coupling between the layers. When an object comes in contact with the sensor, the acoustic coupling is changed, and the output signal amplitude is consequently changed. Depending on the frequency of stimulation and the amount of contact force, the acoustic coupling may be dampened or enhanced, and the output signal amplitude is reduced or increased, respectively. By multiplexing the stimulated points on the driving layer—not the signal from the sensing layer—absolute knowledge of when the signal is produced is preserved, without the inherent "dead time" associated with output signal multiplexing. By noting the amplitude of the output signal, the amount of applied force can be determined, and by correlating the multiplexing address to the output signal, the shape of the contacting object can be determined. Even though time multiplexing with row and column addressing was used in the present design, frequency multiplexing can be applied, as well, to obtain the tactile information.

BRIEF DESCRIPTION OF THE DRAWINGS

FIG. 7 is divided into two sections, FIGS. 7A and 7B, which together illustrate the output characteristics.

DETAILED DESCRIPTION AND PREFERRED EMBODIMENT

Figure 1:
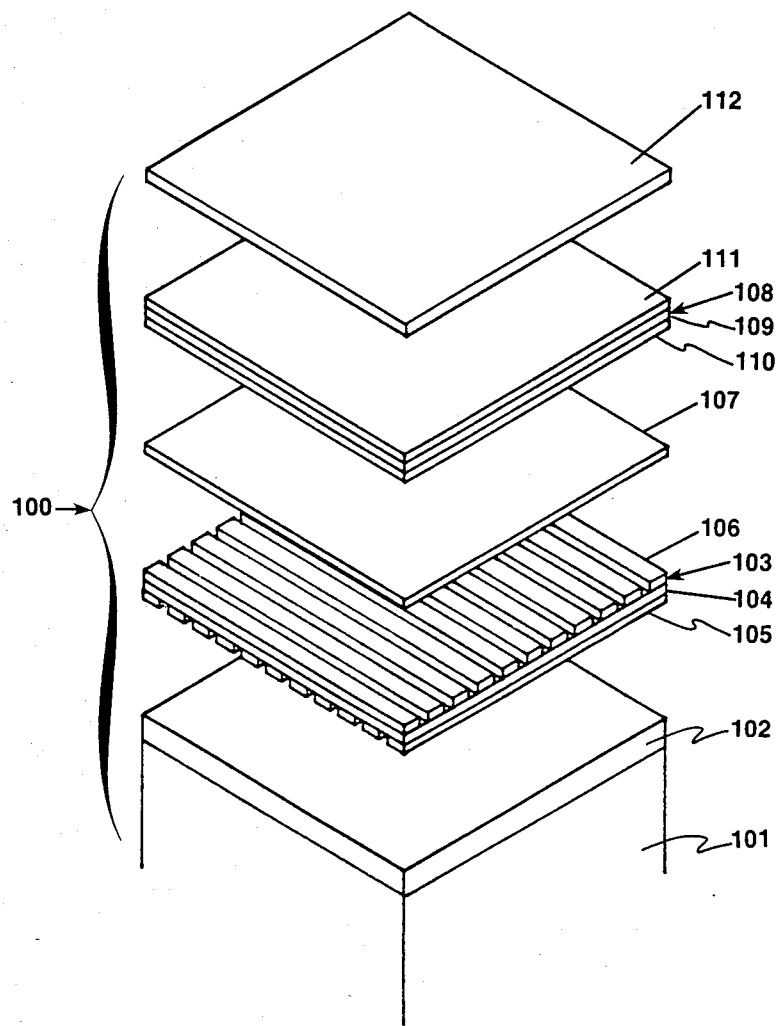
FIG. 1 illustrates, in semischematic form, one embodiment of the tactile sensor of the invention.
Figure 2:
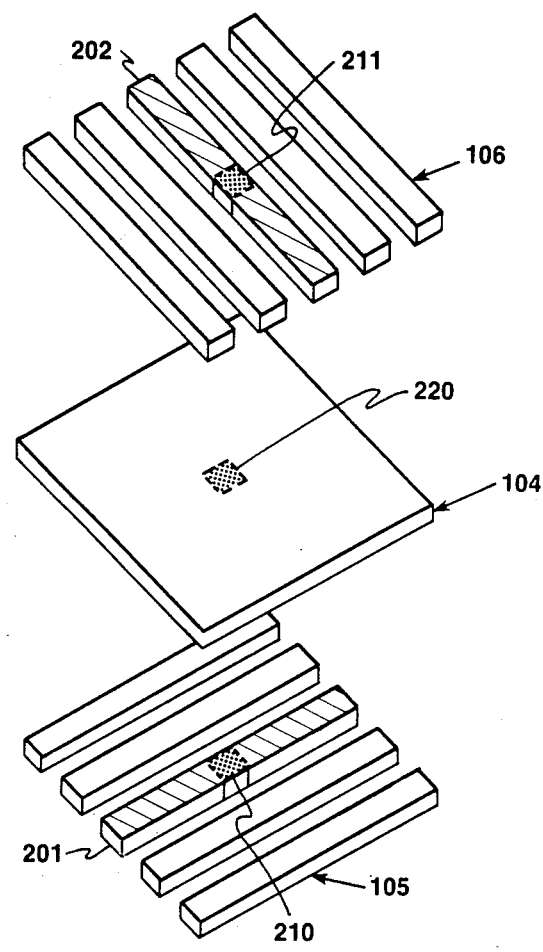
FIG. 2 illustrates an embodiment of electrodes used in the energizing layer.
Figure 3:
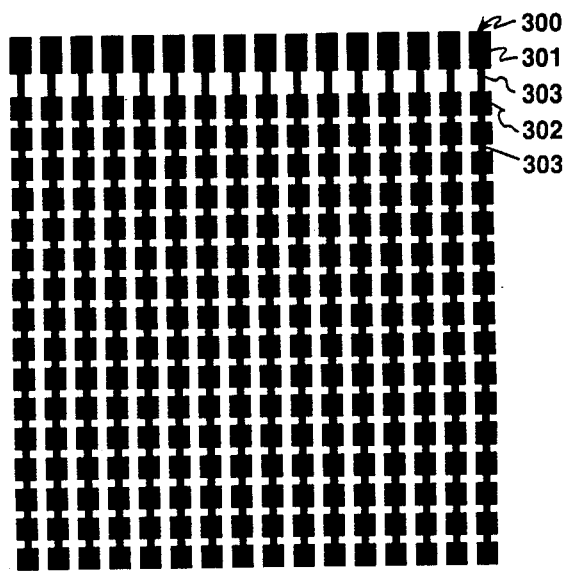
FIG. 3. illustrates a top view of one embodiment of the arrangement of conductors of the energizing layer.
Figure 4:
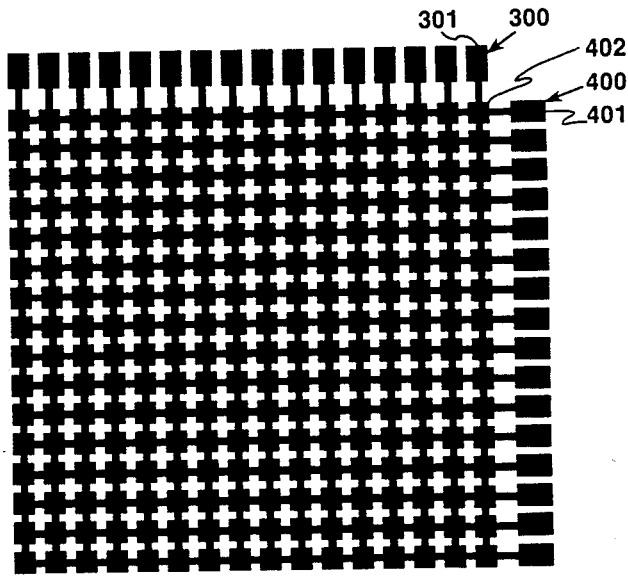
FIG. 4 illustrates a top view of one embodiment of the superposition of the two layers of electrodes used in the energizing layer.

FIG. 1 illustrates one embodiment of the tactile sensor 100. This embodiment comprises a base material 101 that is preferably nonresilient. This base surface may be flat or of arbitrary curvature. If desired a resilient material 102 may be placed adjacent to the base material 101; however, this is optional. An energizing layer 103 is disposed adjacent to the base 101 or optional resilient material 102. Layer 103 is composed of electrodes 105 and 106 on two opposing surfaces of piezoelectric material 104. Electrodes 105,106 may be parallel arrays of electrode bars or conductors as in FIGS. 1 and 2 or as interconnected discrete pads as shown in FIGS. 3 and 4. The electrode bars 105,106 are arranged so that they run at right angles and produce an array of surfaces where the surface of one bar is opposite that of another. These surfaces 210,211 stimulate the active site 220. This surface 220 is the active site as explained below and as shown in FIG. 2. Adjacent to the electrodes 106 is an insulator 107. Insulator 107 may be composed of an insulating sheet or may be of an insulating adhesive. Preferred embodiment is less than 1/32 inch latex rubber coated with resilient adhesive on both sides. A second piezoelectric sensing layer 108 is positioned adjacent to the insulating layer 107. This sensing layer 108 is composed of a piezoelectric material 109 with a conductor 110,111 on opposing surfaces. This piezoelectric sensing layer 108 is preferably resilient. Finally, an optional resilient protective layer 112 may be used to protect the sensor 100 from the environment.

FIG. 2 illustrates in an exploded view the arrangement of the energizing layer 103 in greater detail. This layer 103 is composed of a plurality of conductors 105 disposed on one surface of layer 103 and a plurality of conductors 106 on the opposite surface. If conductors 201 and 202 are energized then an energizing area 220 is defined. The energizing area is produced whenever portions of conductors 105,106 are formed at opposing surfaces. Applying an energizing signal to the appropriate conductors through a multiplexer 505 energizes the device.

FIG. 3 illustrates a preferred embodiment of one set of electrodes 105,106 of the apparatus. A typical electrode 300 is constructed of connecting pad 301 and individual electrode pads 302 that define energizing areas 220. External electrical connection is made to the connection pads 301 and electrode pads 302 by lead connections 303.

FIG. 4 illustrates a top view shows a preferred embodiment of one embodiment of electrodes 105,106 as they would be arranged when superimposed on opposite surfaces of piezoelectric energizing layer 104. Thus electrodes 300 are placed at right angles to electrodes 400. The overlaps of two electrode pads 402 defines an energizing area 220.

One of the great advantages of the invention is that the number of electrical connections required is greatly reduced, for a given number of energizing areas. Conversely, for a given number of electrical connections the number of energizing areas is greatly increased. For example, in a rectangular array as illustrated in FIG. 4 where N is the number of connections along the horizontal axis and M is the number of connections along the vertical axis, $N+M$ connections allow $N \times M$ energizing areas. Thus the particular embodiment shown in FIG. 4 where $N=16$ and $M=16$, 32 connections allow 256 energizing areas.

These energizing areas correspond to sensing areas in the sensing layer. These sensing areas are spatially located on the sensing layer in the same manner as the energizing areas on the energizing layer. Only pressures located at a point corresponding to the sensing energizing area will be measured as further discussed below.

The pattern or layout of the conductors and pads may be rectilinear as shown in FIGS. 1–6 or be in a circular or in any arbitrary shape providing sensing information specific to the desired application.

Figure 5:
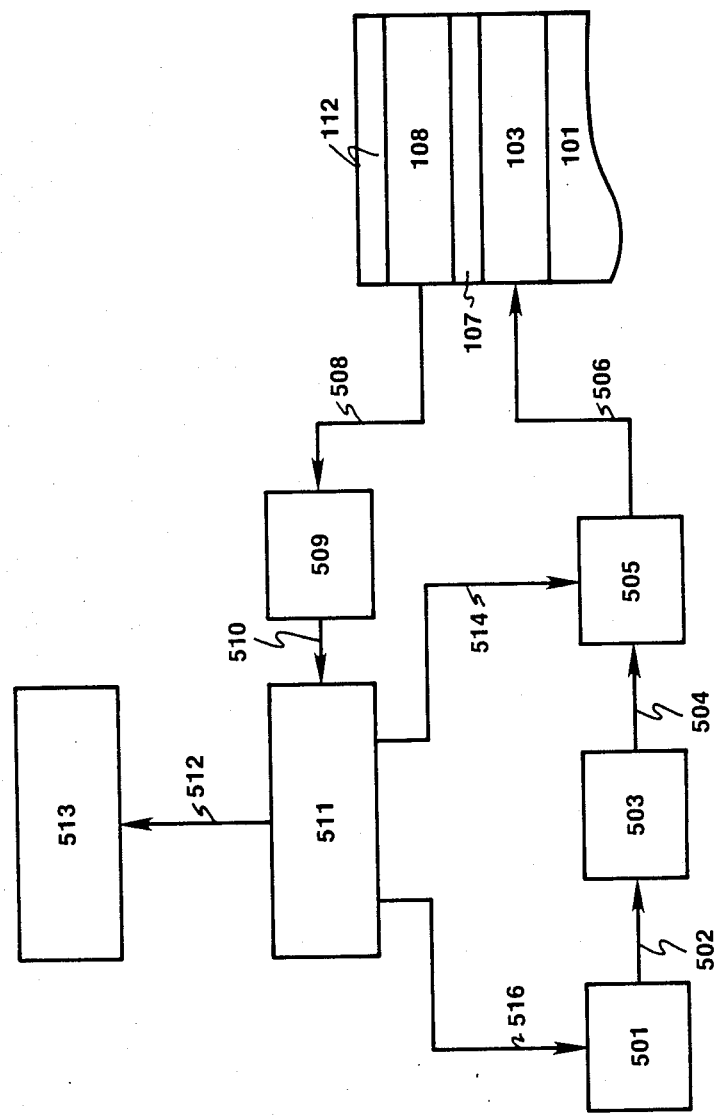
FIG. 5 illustrates one embodiment in semischematic form of the arrangement of various electronic devices to the apparatus of FIG. 1.

FIG. 5 illustrates one embodiment of the electronics associated with the tactile sensor 100. Signal generator 501 is connected to amplifier 503 by leads 502. The amplifier 503 is in turn connected to switching means or multiplexer 505 by leads 504.

Signal input to the tactile sensor apparatus 100 is through electrical connecting leads 506. Leads 506 may be $N+M$ in number where the conductors in the energizing layer are adapted to provide $N \times M$ array of energizing areas 220 in the embodiment of FIG. 1. Leads 506 may number an additional $P+Q$ for an $P \times Q$ array in the embodiment of FIG. 6 discussed below. The output signal from the sensing layer 108 is directed to amplifier 509 by leads 508. The output of amplifier 509 is sent to a signal processing means 511 by leads 510. Signal processing means 511 converts the information contained in the signal of amplitude and frequency to display and/or control apparatus 513 by leads 512. Leads 514 and 516 from the signal processor 511 are optional being required only if the switching means or multiplexer 505 and oscillator 501 are to be controlled by information from the signal processing means 511.

Optionally electrical switching means or multiplexer 505 and leads 506 may be built with the tactile sensor 100 as one unit. This would provide lower wiring complexity and reduce signal interference from other devices. The switching means 505 may be optionally mounted on the base 101 of the apparatus or other suitable place. The oscillator 501 may be fixed or variable in frequency.

In general the apparatus of the invention may be described as comprising a piezoelectric energizing layer 103 having a plurality of conductors 105 disposed on one surface of a piezoelectric material 104 and a plurality of conductors 106 disposed on the opposite surface of the piezoelectric material 104, the plurality of conductors 104,105 having electrical connections 301,401 adapted to be connected to electrical energizing means (not shown); an electrical insulating layer 107 disposed adjacent the piezoelectric energizing layer 103; and a piezoelectric sensing layer 108, having conducting surfaces 110,111 disposed on opposite surfaces thereof, and disposed adjacent the insulating layer 107. Details of the above device include: conductors in the piezoelectric energizing layer 103 that are to provide N×M energizing areas with N+M electrical connections to the energizing layer 103, wherein N×M>1; electrical energizing means for driving said energizing layer and electrical processing means for processing signals from the piezoelectric sensing layer 108 and a switching means or multiplexer adapted to be connected to the N+M electrical connections and adapted to energize the N×M energizing areas.

A further detailed description of the sensor 100 would include: a first electrode layer 105 having N electrodes 201, where N≧1; a first piezoelectric polymer layer 104 disposed adjacent to the first electrode layer 105; a second electrode layer 106 having M electrodes 202, where M≧1; and disposed adjacent to the first piezoelectric polymer layer 104 wherein N×M>1; an insulating layer 107 disposed adjacent to the second electrode layer 106; a first conductive layer 110 disposed adjacent to the insulating layer 107 and adapted to be connected to output processing means; a second piezoelectric polymer layer 109 disposed adjacent to the first conductive layer 110; and a second conductive layer 111 disposed adjacent to the second piezoelectric polymer layer 109 and adapted to be connected to output processing means.

As mentioned previously the apparatus may optionally have a base material 101 which is typically rigid but may have another resilient layer 102 thereon. Likewise a protective layer 112 is disposed adjacent to the piezoelectric sensing layer. This protective layer 112 must be resilient to transmit forces to the sensing layer 108.

Figure 6:
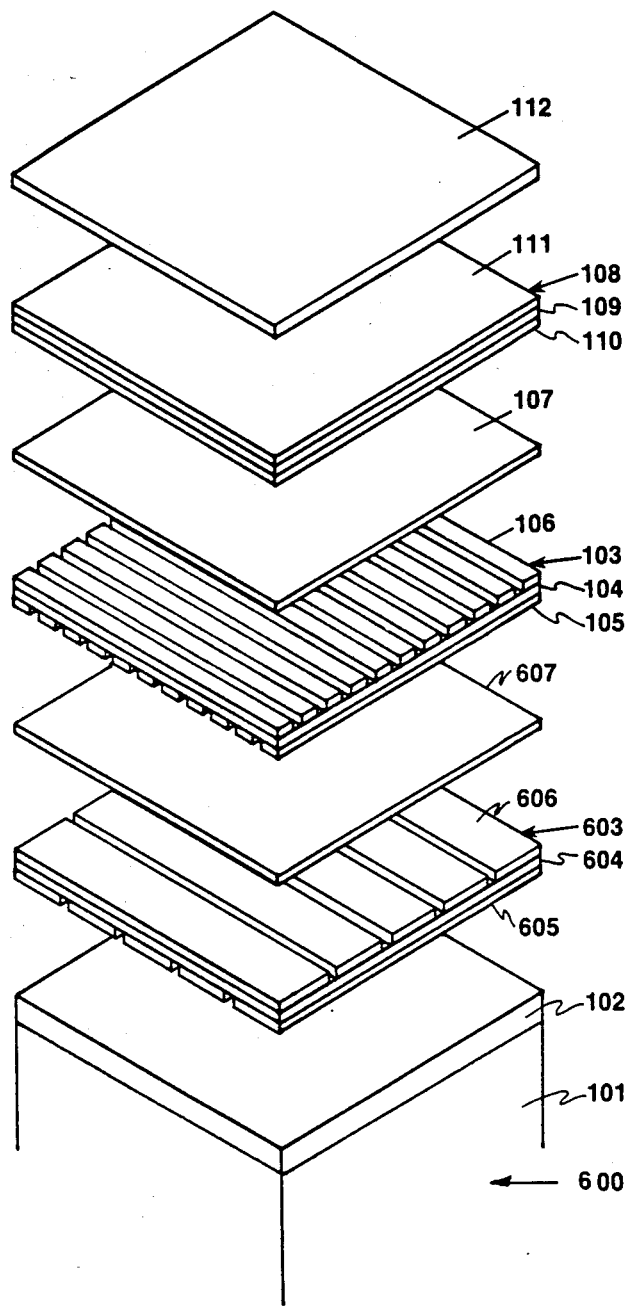
FIG. 6 illustrates in semischematic form another embodiment of the invention wherein two energizing layers are used.

FIG. 6 illustrates another embodiment of the invention wherein an additional piezoelectric energizing layer 603 is added. This embodiment 600 comprises a first electrode layer 605 having N electrodes 201, wherein N≧1; a first piezoelectric polymer layer 604 disposed adjacent to the first electrode layer 605; a second electrode layer 606 having M electrodes 202, wherein M≧1, and disposed adjacent to the first piezoelectric polymer layer 604; a first insulating layer 607 disposed adjacent to the second electrode layer 606; a third electrode layer 105 having P electrodes 201, wherein P≧1, and disposed adjacent to the insulating layer 607; a second piezoelectric polymer layer 104 disposed adjacent to the third electrode layer 105; a fourth electrode layer having Q electrodes 202, wherein Q≧1, and disposed adjacent to the second piezoelectric polymer layer 104, wherein P×Q>1; a second insulating layer 107 disposed adjacent to the fourth electrode layer 106; a first conducting layer 110 disposed adjacent to the second insulating layer 107 and adapted to be connected to output signal processing means; a third piezoelectric polymer layer 109 disposed adjacent to the first conducting layer 110; and a second conductive layer 111 disposed adjacent to the third piezoelectric polymer 109 and adapted to be connected to output processing means. Optionally, a protective layer 112 may be used as well as a base 101 and resilient layer. As can be seen, an additional piezoelectric energizing layer 603 and insulating layer 607 have been added to the basic design of FIG. 1 and second electrode layers 605,606 are adapted to provide N×M energizing areas 220 in the first piezoelectric polymer layer 603 with N+M electrode connections; and the third and fourth electrode layers 105,106 are adapted to provide P×Q energizing areas 220 in the second piezoelectric layer 103 with P+Q electrode connections. Switching means or multiplexer 505 are connected to the N+M and P+Q electrode connections in a manner adapted to energize the appropriate N×M and P×Q energizing areas.

FIG. 6 may also be described as: a first piezoelectric energizing layer 603 having a plurality of conductors 201 disposed on one surface of a piezoelectric material 604 and a plurality of conductors 202 disposed on the opposite surface of the piezoelectric material 604, the plurality of conductors 201,202 having electrical connections 301,401 adapted to be connected to electrical energizing means; a first electrical insulating layer 607 disposed adjacent the first piezoelectric energizing layer 603; a second piezoelectric energizing layer 103 having a plurality of conductors 201 disposed on one surface of a piezoelectric material 104 and a plurality of conductors 202 disposed on the opposite surface of the piezoelectric material, the plurality of conductors 201,202 having electrical connections 301,402 adapted to be connected to electrical energizing means; second electrical insulating layer 107 disposed adjacent the second piezoelectric energizing layer 103; a piezoelectric sensing layer 108 having conducting surfaces 110;111 disposed on opposite surfaces thereof that is disposed adjacent the second insulating layer 107.

Another embodiment of the invention involves the use of two sensing layers rather than the single sensing layer 108 illustrated in FIGS. 1 and 6. This additional sensing layer 108' (not illustrated) would be disposed adjacent to the existing piezoelectric sensing layer 108 with an additional insulating layer 107' between them. This additional sensing layer can be used in the embodiments illustrated in FIGS. 1 and 6. The additional layer would allow a gradation in sensing capability with one layer sensing smaller forces than the other.

This second piezoelectric sensing layer having conducting surfaces on opposite surfaces thereof, and disposed adjacent a second insulating layer may be adapted to have electrical and mechanical characteristics different from the other piezoelectric sensing layer. The layer sensing the lower forces would be preferably placed uppermost in the sensor.

The device is contemplated to operate with variable frequency inputs as further discussed below. D.C. operation of the energizing layer of the apparatus does not appear practical since the piezoelectric layers have insufficient response to D.C. voltages. For example, refering to FIG. 1, for both D.C. and A.C. operation the passive and primary sensing element is the outer most layer of PVF$_2$, layer 108. When an object exerts pressure on the sensor's surface, an output signal is generated. To determine the objects characteristics as for example the shape of the object, single perpendicular pairs of conductors on the first $PVF_2$ layer are energized with a voltage. If the object is not present over the junction of the perpendicular conductors, the second piezoelectric film will simply expand slightly with no consequent output signal. However, if the object is present, the sensing layer will be compressed and an output signal will be registered. Thus, by actively interrogating the N×M perpendicular pairs the shape of the object could be determined.

Another limitation of D.C. excitation of the energizing layer is the mechanical coupling between the two $PVF_2$ layers through the insulating film. If a 30 volt source (±15 VDC, standard for many integrated analog circuits) is applied to the perpendicular conductors, this energizing voltage will generate an electric field within the $PVF_2$ film that causes a thickness expansion of approximately ten angstroms (10 Å). In order to accurately transmit this strain to the sensing film, the insulating layer 107 must be either infinitely rigid or be moderately rigid and have thicknesses on the order of this minute displacement. Even if the D.C. energizing voltage is increased to, say, 200 V and the displacement increased to 66 Å, the thickness of the insulating material is not practical. As a result acoustic coupling and an A.C. mode of energizing operation is preferred.

The device is operated by providing a tactile sensor 100 having a piezoelectric energizing layer 103 with N×M energizing areas 220 and N+M connectors 301,401 for the energizing areas 201 and having a piezoelectric sensing layer 108 adjacent to the energizing layer 103 and electrically insulated therefrom; providing a variable frequency electrical signal at a frequency and amplitude adapted to energize the energizing areas 220; switching the signal to the N+M connectors in a manner adapted to energize selected energizing areas 220 of the energizing layer 103 in a predetermined sequence; and processing a signal generated by the sensing layer 108 to determine the characteristics of an object that is touching the sensing layer 111 or protective layer 112. The energizing of selected energizing areas 220 may be in a predetermined sequence in an algorithm driven sequence; in a random sequence. An algorithm may be used that provides low spatial resolution and reverts to high resolution when an object is sensed. The method can be adapted to processing a signal from the sensing layer that determines characteristics of an object touching the device or sensing layer such as force, shape of the object or weight.

The method would be similar for the alternate embodiment of the tactile sensor 601; again one is switching the signal to the connectors 301,401 in a manner adapted to energize selected energizing areas 220 of the energizing layers 103,603 in a predetermined sequence and processing the signal generated by the sensing layer to determine the characteristics of an object touching the sensing layer.

The signal generated in the sensing layer of the tactile sensor apparatus will vary in frequency and amplitude; by processing the frequency and amplitude information in the signal from the sensing layer characteristics of an object in contact with the sensor can be determined.

Another method of operation is that of monitoring. While in the monitor mode the energizing layer is inactive. The output of the sensing layer 111 is monitored for a given change in signal. When a signal is detected the energizing system is activated and normal operation resumes. This method may be described in more detail as providing a tactile sensor having a piezoelectric energizing layer with N×M energizing areas and N+M connectors for the energizing areas and having a piezoelectric sensing layer adjacent to the energizing layer and electrically insulated therefrom; providing electrical signal energizing and output processing means; monitoring the electrical output of the sensing layer to determine if an object is in contact with the tactile sensor while keeping the energizing layer and electrical signal energizing means inactive; switching the tactile sensor system to active status when an output signal is sensed from the sensing layer; providing an alternating frequency electrical signal at a frequency and amplitude adapted to energize the energizing areas; switching the signal to the N+M connectors in a manner adapted to energize selected energizing areas of the energizing layer in a predetermined sequence; and processing a signal generated by the sensing layer to determine the characteristics of an object that is touching the tactile sensor.

EXAMPLES 1–4

For these examples tests were done at the following forces 0,5,10, and 50 g on the sensor.

The sensor was constructed in a ¼ inch×¼ inch configuration. A ⅜ inch thick rigid plastic to which was bonded a 1/16 inch thick rigid platform was used for the base material. A 1/32 inch thick latex rubber material was placed over the base. The piezoelectric energizing layer and piezoelectric sensing layer (¾ inch by 1½ inches) were both cut from the same $PVF_2$ stock sheet material. Because of previous problems with separation of metallization on the layers both ¼ inch wide strips (approximately 1½ inches long) of metallization $PVF_2$ were cut from a stock sheet so that the grain of metallization/polymer ran parallel to the length of the strips. A 20:1 mixture of polyurethane adhesive was prepared by adding one small drop of Tycel 7200 (Lord Corporation) curing agent to 0.5 ml of Tycel 7000 adhesive. The mixture was stirred for about 1 minute and applied to the end of each strip on one side with a brush to lay down a good insulating layer. The adhesive was allowed to dry overnight. A second batch of adhesive was made and applied to one of the previously coated surfaces. The second strip was laid on top of the first so that the two coated surfaces bonded to each other with an overlap of ¼ inch. The layers were pressed together and allowed to dry.

Because of heating problems while curing the wire bonding adhesive, the wire leads were first attached to the $PVF_2$ strips before constructing the sensor. Wire-wrap wire was bared approximately 3 mm and laid against the metallized surface near one end of the $PVF_2$ strip. A drop of silver epoxy paste, mixed in a 1:1 ratio was dabbed on this junction and heat cured under a heat lamp for 1½ hours at 80° C. This makes a solid bond with excellent electrical conductivity. A second wire was attached to each strip on the opposite side near the same end using the same technique.

Figure 7:
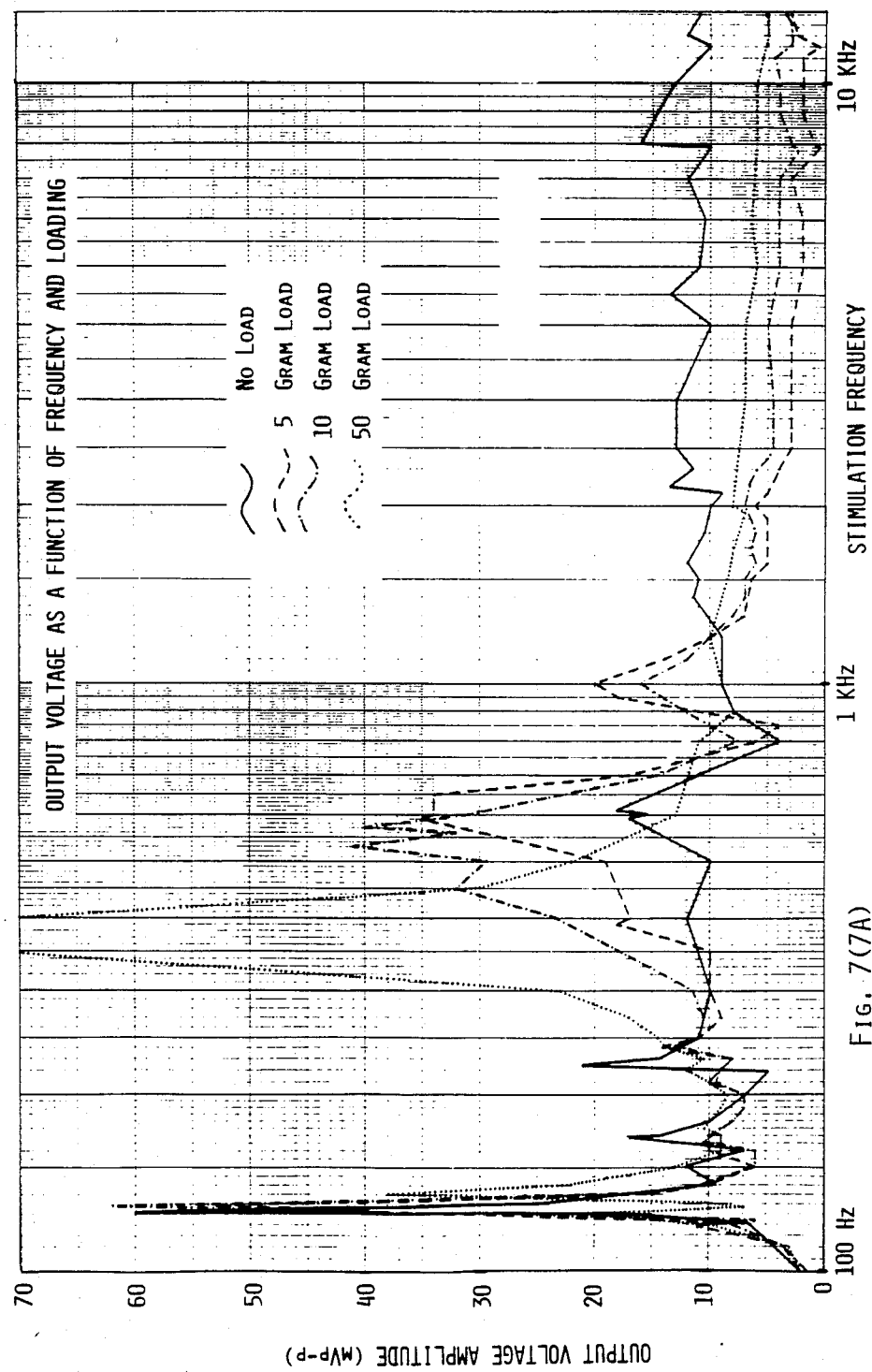
FIG. 7 illustrates the typical output characteristics of the tactile sensor.
Figure 7:
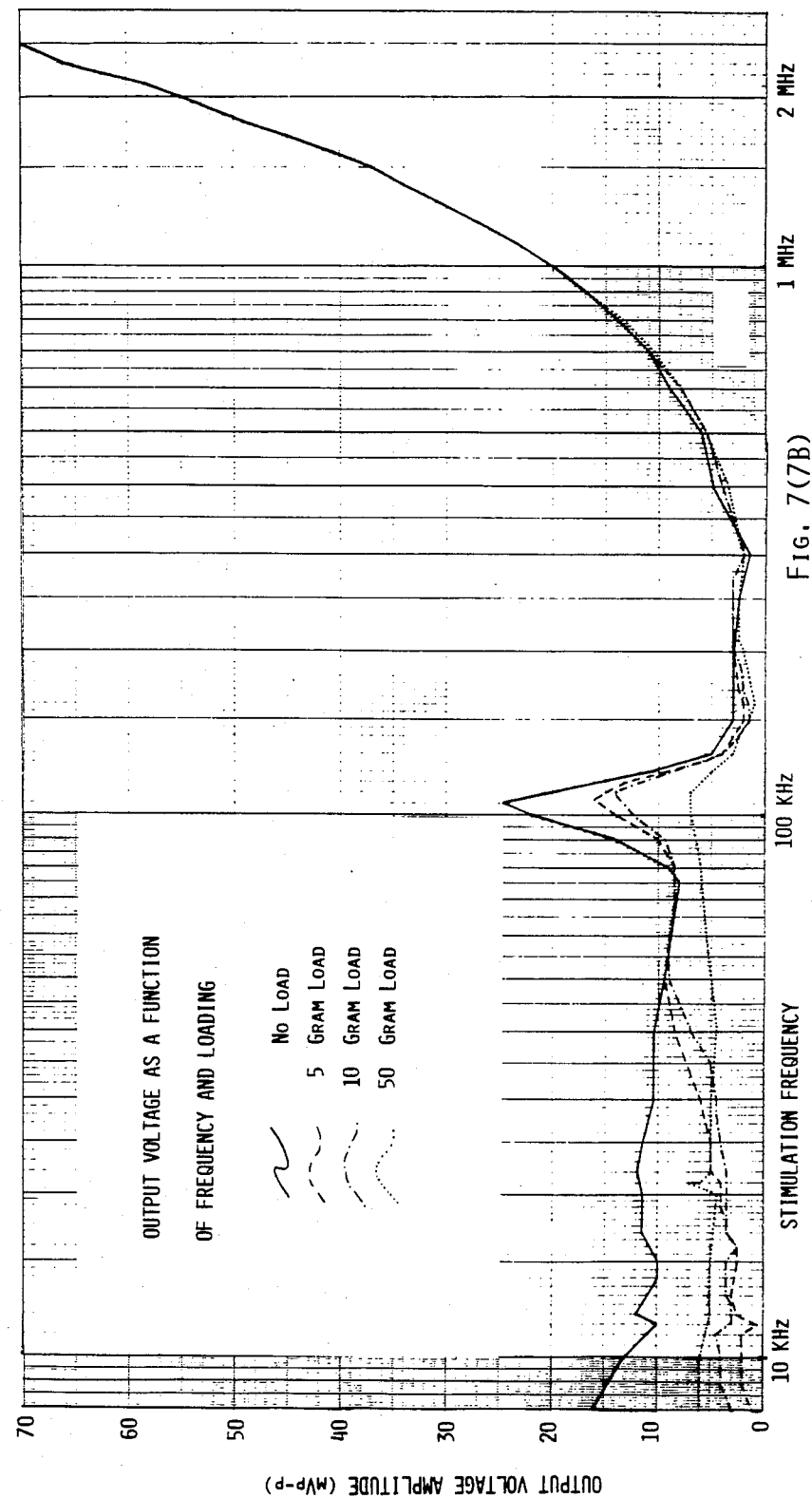

The finished sensor was then clamped using two insulated paper clips with magnetic bases and stretched across the latex and base above. 0.3 inch×0.3 inch contact areas were used for the weights. Detailed output signal measurements were made for a wide range of stimulation frequencies for the structure unloaded and loaded with 5 g, 10 g, or 50 grams. The data is plotted in a single graph in FIG. 7 so that comparisons can easily be made.

Test Conditions: Input voltage—10 VAC; output voltage bandwidth limited to 20 MHz to reduce the amount of noise content in the signal; load=0,5,10,50 gm; frequency range: 100 Hz to 10 MHz; output voltage measured in mV peak-to-peak (mvpp).

This series of tests and the resulting graph of data (FIG. 7) reveal considerable information on the tactile models of the device. Clearly, several different trends are seen in terms of response to loading. These are examined below.

First of all, both increased coupling and dampening modes are observed. At 105–110 KHz, a strong resonance is observed with increased monotonic dampening of the output response seen as the loading is increased.

In the frequencies between 2 KHz and 10 KHz, the increased coupling mode is observed for forces above and including 5 gram, while the dampening mode dominates in the 0–5 gram range; hence, the tactile mode is dependent on both frequency and loading. Two frequency crossover points between coupling and dampening modes are clearly visible. A very sharp crossover occurs at 1.2 KHz where all three loaded data curves intersect at a single point. The second frequency crossover is considerably broader and occurs in the 22 KHz–34 KHz range.

The second main observation is that frequency shifts in resonance as a function of loading. In the 126–135 Hz range, the first resonance observed, a slight upward shift in resonance correlated with increased force is observed. The same is true for the 105 KHz–110 KHz resonance discussed previously. However, the most drastic and noteworthy is a shift that begins at 610 Hz under no load and ends up at 370 Hz for a 50 gram load. Not only does the resonant frequency shift, but the amplitude increases dramatically. The table below shows the summary data points of these phenomena:

| Loading | Output Amplitude (mv pp) | Resonant Frequency |
|---------|--------------------------|---------------------|
| 0       | 18                       | 610                 |
| 5       | 35                       | 590                 |
| 10      | 41                       | 530                 |
| 50      | 90                       | 370                 |

From this response, it is apparent that the loading mass plays an important role in the resonant response of the device by moving in harmony with the piezoelectric (PVF$_2$) structure. Like a vibrating string, the PVF$_2$ structure resonates at a frequency that is a function of mass. As the mass increases, the resonant frequency decreases. The increase in amplitude is probably due to increased coupling between the energizing and sensing layers of PVF$_2$.

To reiterate, the phenomenon seen here is that the data points for the loaded device show a monotonic relationship at a given frequency. But, the data points for the unloaded device do not necessarily follow the same trend. This is because the response is a function of loading, and the data in FIG. 7 includes only loads in 5–50 gram range. In any case, the data presented here indicate strong amplitude and frequency correlations of output signal to loading.

Obviously, by performing a spectral analysis of a wide band of stimulation frequencies, the precise loading could be determined and the range of possible loads may even be broadened. However, to perform such an analysis is expensive and time consuming. To develop a sensor that responds relatively quickly, say 1–10 msec for the entire array, and is not hardware intensive, it is better to examine a single or a few key frequencies rather than the entire spectrum.

The last point to be made concerns capacitive coupling between the PVF$_2$ layers. This coupling is always present to some extent, however, as the stimulation frequency increases, the coupling increases and eventually dominates the system so that no tactile response is observed.

In our test conditions, the coupling effect was noticeable around 300 KHz, was definitely dominating the data at 700 KHz, and was the only signal observed at 900 KHz. In fact, for stimulation frequencies of 900 KHz and above, there were no observable differences in the output signal level for various loadings. And as expected, as capacitive coupling increased, so did the output signal level.

Thus, in general, the PVF$_2$ structure must be stimulated with a signal whose frequency is well below the point where capacitive coupling interferes with the tactile response signal.

EXAMPLE 5

To further document the invention the oscilloscope signals for the sensor configuration used in Examples 1–4 were monitored.

The dampening mode tactile response was distinctly evident and apparent for the range of loads from 0 to 50 grams. The change in output voltage is a non-linear function of loading, but nonetheless, it is strongly correlated to the loading.

A phase shift phenomenon was also observed. This characteristic has been observed by other researchers investigating the tactile response of PVF$_2$. The amount of phase shift may be correlated to the time of travel for an acoustic signal to propagate across the flexible adhesive layer. As loading is applied to the structure, the device becomes more tightly pressed, and the distance between the PVF$_2$ layers becomes less. Thus, the time to travel and the phase shift becomes less.

The response to a sinusoidal input at resonance (105 KHz) shows the dampening mode response and a sensitivity to loads as small as one gram. Although the change in output amplitude as a function of loading is not linear, the two parameters are correlated.

EXAMPLE 6

The response of the sensor to a 10 KHz square wave input was tested. This frequency was chosen because this frequency lies in the region where previously the unloaded response did not appear to correlate to the trend established by the loaded (5, 10, and 50 g) response data.

The most obvious response to the square wave input is the characteristic piezoelectric response of a decaying sinusoid, which begins with a sharp spike in response to the step stimulation and exponentially decays. Superimposed on the exponential decay is resonant ringing. As expected, the resonance was observed to ring at approximately 100 KHz.

As the device was loaded under this stimulation condition, two important changes were observed in the output. First, the resonant spike and ringing continuously decreased as the loading increased. This was expected from the data in FIG. 7. More importantly, the low frequency (10 KHz) response, was also affected.

For small loading (up to 5 grams), the load dampened the output response. The output resembled a square wave, with the amplitude decreased with increasing loading until at approximately 5 grams only the resonant response could be seen. The amplitude of the low frequency stimulation and response had practically vanished.

As the loading continued to increase, an interesting reversal took place, and the output began to resemble a square wave in phase with the input. Thus, the increased coupling mode began to dominate the system, and the output signal increased with loading. For 30 g loading, the resonant ringing had almost disappeared, and the low frequency response was similar to the input. The total response to loading shows a smooth drop from 12 mvpp to zero in square wave output for the load range 0–5 grams followed by an increase in output signal to an asymptote at approximately 5 mvpp. We have chosen to call the force applied when minimum signal output is observed the load crossover point.

The load crossover point between the increased coupling mode and the dampening mode is approximately 4½ grams of loading for the 10 KHz square wave. This crossover point shifts up or down depending on the stimulation frequency. For example, at 100 KHz–105 KHz the crossover point has shifted upward to an undetermined point so that only the dampening mode is seen for loads in the 0–50 gram range.

One useful application of this frequency-dependent response is the incorporation of multiple sampling frequencies to dynamically change sensitivity without changing geometry or to verify a response at one frequency by correlation of the response at another frequency, hence increasing the sensor's accuracy.

A preferred bonding or adhesive material for the tactile sensor is Tycel ® 7000 urethane laminating adhesive combined with 7200 Series curing agent in a ratio of 20:1 adhesive to curing agent (Hughson Chemicals, Lord Corporation, 2000 West Grandview Blvd., Erie, Pa. 16512). Of course any material of similar characteristics can also be used. This nonconducting material is resilient and is used for bonding the various layers of the sensor together. The above adhesive had the appropriate bonding qualities necessary to bond the various layers of the sensor to each other while simultaneously providing good acoustic coupling between the layers. It is essential that each of the layers of the tactile sensor be properly bonded to the adjacent layers to provide good acoustic coupling between layers.

A preferred embodiment for the insulators (e.g. 107) is a very thin layer of less than 1/32 inch thickness latex rubber coated with a resilient adhesive.

As mentioned earlier the piezoelectric layers are preferably a piezoelectric polymer such as $PVF_2$ and are in the form of a thin film the electrodes being formed or etched thereon on in ways generally known in the art. Preferably the electrodes are vapor deposited.

Electrical contact to the electrodes or conductors of the piezoelectric sensing and energizing layers is preferably with a silver epoxy although other materials known in the art may be used. An example of preferred electrical conducting epoxy is EPO-TEK ® H20E (Epoxy Technology Inc., 14 Fortune Drive, Billerica, Mass. 01821) although any similar silver filled epoxy such as those designed for chip bonding in microelectronic and optoelectronic applications may be used. The H20E epoxy used requires heat treatment; thus, temperature should be kept below the temperature where the piezoelectric material would lose its electrical polarization. For $PVF_2$ this temperature should be below 120° C. A temperature of 80° C. was found to be suitable.

The leads are preferably attached to the piezoelectric layers of the sensor prior to assembly with the nonconducting adhesive used to hold the various layers together. This allows subsequent assembly steps at room temperature and avoids elevated temperatures that would affect the nonconducting adhesive.

As mentioned previously polyvinylidene fluoride ($PVF_2$) is the preferred piezoelectric material. It should have its electrical polarization oriented in the thickness direction. Preferred thickness of the piezoelectric material using $PVF_2$ is approximately 28 $\mu$m. This is a medium size thickness that optimizes the motor and generator responses (mechanical reaction to electrical stimulus and electrical reaction to mechanical stimulus) of $PVF_2$. Other usable thicknesses range from a few micrometers to as large as several millimeters.

Input voltages to the energizing electrical energizing layer 103 of the tactile sensor 100 by an oscillator 501 may be fixed, variable, sinusoidal square or a suitable arbitrary wave form of single or multiple frequencies. A square wave of 1 KHz–10 KHz was found to provide adequate information about the sensor response at the fundamental frequency and higher harmonics and to provide adequate information for ambiguously identifying the force applied to the tactile sensor from an unknown load.

The invention solves another problem common to cross point arrays—the phantom point. For example in an N=2 by M=2 array of conductors there are N×M=4 points. If however three of these points are energized simultaneously the fourth point cannot be determined to be on or off. Output signals would be the same in either case. The invention avoids this problem by addressing each point independently in time by the switching means or multiplexer 505.

While the forms of the invention herein disclosed constitute presently preferred embodiments, many others are possible. It is not intended herein to mention all of the possible equivalent forms or ramifications of the invention. It is to be understood that the terms used herein are merely descriptive rather than limiting, and that various changes may be made without departing from the spirit or scope of the invention.

We claim:

1. A tactile sensing apparatus comprising:
   a. a piezoelectric energizing layer having a plurality of conductors disposed on one surface of a piezoelectric material and a plurality of conductors disposed on the opposite surface of the piezoelectric material, the plurality of conductors having electrical connections adapted to be connected to electrical energizing means;
   b. an electrical insulating layer disposed adjacent the piezoelectric energizing layer; and
   c. a piezoelectric sensing layer, having conducting surfaces disposed on opposite surfaces thereof, and disposed adjacent the insulating layer.

2. The apparatus of claim 1 further comprising a protective layer disposed adjacent to the piezoelectric sensing layer.

3. The apparatus of claim 1 wherein the conductors in the piezoelectric energizing layer are adapted to provide N×M energizing areas with N+M electrical connections to the energizing layer wherein N×M>1.

4. The apparatus of claim 3 further comprising electrical energizing means for driving the energizing layer and electrical processing means for processing signals from the piezoelectric sensing layer.

5. The apparatus of claim 4 wherein the electrical energizing means further comprises:
   a. a variable frequency oscillator;
   b. an amplifier coupled to the oscillator;
   c. a multiplexer coupled to the amplifier and coupled to the energizing layer; and
   d. a signal processor coupled to the variable frequency oscillator and multiplexer; and wherein the electrical processing means further comprises an output amplifier coupled to the signal processor that is in turn coupled to signal output means.

6. The apparatus of claim 3 further comprising a multiplexer adapted to be connected to the N+M electrical connections and adapted to energize the N×M energizing areas.

7. The apparatus of claim 6 further comprising electrical energizing means adapted to energizing the multiplexer and electrical processing means adapted to processing signals from the piezoelectric sensing layer.

8. The apparatus of claim 7 wherein the electrical energizing means further comprises: a variable frequency oscillator coupled to the multiplexer and a signal processor; and wherein the electrical processing means further comprises the signal processor coupled to the piezoelectric sensing layer.

9. The apparatus of claim 7 wherein the electrical energizing means further comprises an oscillator and wherein the electrical processing means comprises a signal processor.

10. The apparatus of claim 9 wherein the oscillator is a variable frequency oscillator.

11. The apparatus of claim 1 wherein the piezoelectric material is $PVF_2$.

12. A tactile sensing apparatus comprising:
   a. a base material;
   b. a piezoelectric energizing layer disposed on the base material having a plurality of conductors disposed on one surface of a piezoelectric material and a plurality of conductors disposed on the opposite surface on the piezoelectric material, the plurality of conductors having electrical connections adapted to be connected to electrical switching means;
   c. an electrical insulating layer disposed adjacent the energizing layer; and
   d. a piezoelectric sensing layer, having conducting surfaces disposed on opposite surfaces thereof, and disposed adjacent the insulating layer, the conducting surfaces adapted to be connected to electrical processing means.

13. The apparatus of claim 12 further comprising a protective layer disposed adjacent to the piezoelectric sensing layer.

14. The apparatus of claim 12 wherein the conductors in the piezoelectric energizing layer are adapted to provide N×M energizing areas with N+M electrical connections to the energizing layer wherein N×M>1.

15. The apparatus of claim 12 further comprising:
   a. electrical energizing means for energizing the piezoelectric energizing layer; and
   b. electrical processing means for processing signals from the piezoelectric sensing layer.

16. The apparatus of claim 12 wherein a piezoelectric material disposed in the piezoelectric energizing and sensing layer further comprises $PVF_2$.

17. The apparatus of claim 12 further comprising a resilient material between the base material and piezoelectric energizing layer.

18. The apparatus of claim 12 further comprising electrical switching means connected to the N+M electrode connections and disposed on the base material.

19. The apparatus of claim 15 wherein the electrical energizing means further comprises an oscillator.

20. The apparatus of claim 18 wherein the electrical switching means comprises a multiplexer.

21. The apparatus of claim 19 wherein the oscillator further comprises a variable frequency oscillator.

22. A tactile sensing apparatus comprising:
   a. a first electrode layer having N electrodes, where $N \geq 1$;
   b. a first piezoelectric layer disposed adjacent to the first electrode layer;
   c. a second electrode layer having M electrodes, where $M \geq 1$, and disposed adjacent to the first piezoelectric polymer layer wherein N×M>1;
   d. an insulating layer disposed adjacent to the second electrode layer;
   e. a first conductive layer disposed adjacent to the insulating layer and adapted to be connected to output processing means;
   f. a second piezoelectric layer disposed adjacent to the first conductive layer; and
   g. a second conductive layer disposed adjacent to the second piezoelectric layer and adapted to be connected to output processing means.

23. The apparatus of claim 22 further comprising a protective layer disposed adjacent to the second conductive layer.

24. The apparatus of claim 22 further comprising a base layer disposed adjacent to the first electrode layer.

25. The apparatus of claim 24 further comprising a protective layer disposed adjacent to the second conductive layer.

26. The apparatus of claim 22 wherein the first electrode layer and second electrode layer are adapted to provide N×M energizing areas in the first piezoelectric layer with N+M electrode connections.

27. The apparatus of claim 23 wherein the first electrode layer and second electrode layer are adapted to provide N×M energizing areas in the first piezoelectric layer with N+M electrode connections.

28. The apparatus of claim 24 wherein the first electrode layer and second electrode layer are adapted to provide N×M energizing areas in the first piezoelectric layer with N+M electrode connections.

29. The apparatus of claim 25 wherein the first electrode layer and second electrode layer are adapted to provide N×M energizing areas in the first piezoelectric layer with N+M electrode connections.

30. The apparatus of claim 26 wherein the piezoelectric layer comprises $PVF_2$.

31. The apparatus of claim 26 further comprising electrical switching means connected to the N+M electrical connections in a manner adapted to energize the N×M energizing areas.

32. The apparatus of claim 29 further comprising electrical switching means connected to the N+M electrical connections in a manner adapted to energize the N×M energizing areas and disposed on the base material.

33. The apparatus of claim 26 further comprising:
a. electrical energizing means for energizing the energizing areas through the N and M electrodes; and
b. electrical output processing means for processing signals from the first and second conductive layers.

34. The apparatus of claim 31 further comprising:
a. electrical energizing means for energizing the energizing areas connected to the multiplexer; and
b. electrical output processing means for processing signals from the first and second conductive layers.

35. The apparatus of claim 34 wherein the electrical energizing means comprises an oscillator.

36. A tactile sensing apparatus comprising:
a. a first piezoelectric energizing layer having a plurality of conductors disposed on one surface of a piezoelectric material and a plurality of conductors disposed on the opposite surface of the piezoelectric material, the plurality of conductors having electrical connections adapted to be connected to electrical energizing means;
b. a first electrical insulating layer disposed adjacent the first piezoelectric energizing layer;
c. a second piezoelectric energizing layer having a plurality of conductors disposed on one surface of a piezoelectric material and a plurality of conductors disposed on the opposite surface of the piezoelectric material, the plurality of conductors having electrical connections adapted to be connected to electrical energizing means;
d. a second electrical insulating layer disposed adjacent the second piezoelectric energizing layer; and
e. a piezoelectric sensing layer having conducting surfaces disposed on opposite surfaces thereof that is disposed adjacent the second insulating layer.

37. The apparatus of claim 36 further comprising a base material disposed adjacent the first piezoelectric energizing layer.

38. The apparatus of claim 37 further comprising a protective layer disposed adjacent to the piezoelectric sensing layer.

39. The apparatus of claim 36 wherein the conductors are adapted to provide N×M energizing areas with N+M electrical connections to the conductors wherein N×M≧1 in the first piezoelectric layer and P×Q energizing areas in the second piezoelectric energizing layer with P+Q electrical connections wherein P×Q≧1.

40. The apparatus of claim 39 further comprising switching means connected to the N+M and P+Q electrical connections in a manner adapted to energize the appropriate N×M and P×Q energizing areas.

41. A tactile sensing apparatus comprising:
a. a first electrode layer having N electrodes, wherein N≧1;
b. a first piezoelectric polymer layer disposed adjacent to the first electrode layer;
c. a second electrode layer having M electrodes, wherein M≧1, and disposed adjacent to the first piezoelectric polymer layer, wherein N×M>1;
d. a first insulating layer disposed adjacent to the second electrode layer;
e. a third electrode layer having P electrodes, wherein P≧1, and disposed adjacent to the insulating layer;
f. a second piezoelectric polymer layer disposed adjacent to the third electrode layer;
g. a fourth electrode layer having Q electrodes, wherein Q≧1, and disposed adjacent to the second piezoelectric polymer layer, wherein P×Q>1;
h. a second insulating layer disposed adjacent to the fourth electrode layer;
i. a first conducting layer disposed adjacent to the second insulating layer and adapted to be connected to output signal processing means;
j. a third piezoelectric polymer layer disposed adjacent to the first conducting layer; and
k. a second conductive layer disposed adjacent to the third piezoelectric polymer and adapted to be connected to output processing means.

42. The apparatus of claim 41 wherein the first and second electrode layers are adapted to provide N×M energizing areas in the first piezoelectric polymer film layer with N+M electrode connections; and wherein the third and fourth electrode layers are adapted to provide P×Q energizing areas in the second piezoelectric film layer with P+Q electrode connections.

43. The apparatus of claim 42 further comprising switching means connected to the N+M and P+Q electrode connections in a manner adapted to energize the appropriate N×M and P×Q energizing areas.

44. The apparatus of claim 42 wherein the switching means comprises a multiplexer.

45. The apparatus of claim 42 further comprising a first multiplexer connected to the N+M electrode connections and a second multiplexer connected to the P+Q electrode connections each adapted to respectively energize the N×M and P×Q energizing areas.

46. The apparatus of claim 1 further comprising:
a. an electrical insulating layer disposed adjacent the piezoelectric sensing layer; and
b. a second piezoelectric sensing layer, having conducting surfaces on opposite surface thereof, and disposed adjacent the second insulating layer and wherein the second piezoelectric sensing layer is adapted to have electrical and mechanical characteristics different from the other piezoelectric sensing layer.

47. The apparatus of claim 22 further comprising:
a. a second insulating layer disposed adjacent to the second conductive layer;
b. a third conductive layer disposed adjacent to the second insulating layer and adapted to be connected to output processing means;
c. a third piezoelectric polymer layer disposed adjacent to the third conductive layer; and
d. a fourth conductive layer disposed adjacent to the third piezoelectric polymer layer and adapted to be connected to output processing means.

48. The apparatus of claim 47 wherein the second and third piezoelectric layers are adapted to have different electrical and mechanical characteristics.

49. The apparatus of claim 41 further comprising:
a. a third insulating layer disposed adjacent to the second conducting layer;
b. a third conducting layer disposed adjacent to the third insulating layer and adapted to be connected to output signal processing means;
c. a fourth piezoelectric polymer layer disposed adjacent to the third conducting layer; and
d. a fourth conducting layer disposed adjacent to the fourth piezoelectric polymer layer and adapted to be connected to signal processing means.

50. The apparatus of claim 49 wherein the third and fourth piezoelectric layers are adapted to have different electrical and mechanical characteristics.

51. A method of operating a tactile sensor comprising:
  a. providing a tactile sensor having a piezoelectric energizing layer with N×M energizing areas and N+M connectors for the energizing areas and having a piezoelectric sensing layer adjacent to the energizing layer and electrically insulated therefrom;
  b. providing an alternating frequency electrical signal at a frequency and amplitude adapted to energize the energizing areas;
  c. switching the signal to the N+M connectors in a manner adapted to energize selected energizing areas of the energizing layer in a predetermined sequence; and
  d. processing a signal generated by the sensing layer to determine the characteristics of an object that is touching the sensing layer.

52. The method of claim 51 whereby the energizing of selected areas in a predetermined sequence is in an algorithm driven sequence.

53. The method of claim 51 whereby the energizing of selected areas in a predetermined sequence is in a random sequence.

54. The method of claim 51 whereby the energizing of selected areas in a predetermined sequence is by an algorithm that provides low spatial resolution and reverts to high resolution when an object is sensed.

55. A method of claim 51 whereby the processing of a signal from the sensing layer is adapted to determine force on the sensing layer.

56. The method of claim 51 whereby the processing of a signal from the sensing layer is adapted to determine the shape of an object touching the sensing layer.

57. A method of operating a tactile sensor comprising:
  a. providing a tactile sensor having a first and second piezoelectric energizing layer with N×M energizing areas and N+M connectors on the first layer and P×Q energizing areas and P+Q connectors on the second layer, further having a piezoelectric sensing layer disposed adjacent to the second energizing layer and electrically insulated therefrom;
  b. providing an alternating frequency electrical signal at a frequency and amplitude adapted to energize the M×N and P×Q energizing areas;
  c. switching the signal to the connectors in a manner adapted to energize selected energizing areas of the energizing layer in a predetermined sequence; and
  d. processing a signal generated by the sensing layer to determine the characteristics of an object touching the sensing layer.

58. A method of operating a tactile sensor comprising:
  a. providing a tactile sensor having a piezoelectric energizing layer with N×M energizing areas and N+M connectors for the energizing areas and having a piezoelectric sensing layer adjacent to the energizing layer and electrically insulated therefrom;
  b. providing a variable frequency electrical signal at a frequency and amplitude adapted to energize the energizing areas;
  c. switching the signal to the connectors in a manner adapted to energize selected energizing areas of the energizing layer in a predetermined sequence;
  d. generating a signal in the sensing layer that varies in frequency, amplitude, in response to an object in contact with the tactile sensor; and
  e. processing the frequency and amplitude information in the signal from the sensing layer to determine the characteristics of the object.

59. A method of operating a tactile sensor comprising:
  a. providing a tactile sensor having a piezoelectric energizing layer with N×M energizing areas and N+M connectors for the energizing areas and having a piezoelectric sensing layer adjacent to the energizing layer and electrically insulated therefrom;
  b. providing a variable frequency electrical signal at a frequency and amplitude adapted to energize the energizing areas;
  c. switching the signal to the connectors in a manner adapted to energize selected energizing areas of the energizing layer in a predetermined sequence and in a manner adapted to eliminate the phantom point problem;
  d. generating a signal in the sensing layer that varies in frequency and amplitude in response to an object in contact with the tactile sensor; and
  e. processing the signal from the sensing layer to determine characteristics of the object.

60. A method of operating a tactile sensor system comprising:
  a. providing a tactile sensor having a piezoelectric energizing layer with N×M energizing areas and N+M connectors for the energizing areas and having a piezoelectric sensing layer adjacent to the energizing layer and electrically insulated therefrom;
  b. providing electrical signal energizing and output processing means;
  c. monitoring the electrical output of the sensing layer to determine if an object is in contact with the tactile sensor while keeping the energizing layer and electrical signal energizing means inactive;
  d. switching the tactile sensor system to active status when an output signal is sensed from the sensing layer;
  e. providing an alternating frequency electrical signal at a frequency and amplitude adapted to energize the energizing areas;
  f. switching the signal to the N+M connectors in a manner adapted to energize selected energizing areas of the energizing layer in a predetermined sequence; and
  g. processing a signal generated by the sensing layer to determine the characteristics of an object that is touching the tactile sensor.

* * * * *